US00PP08933P

United States Patent [19]

Imazio

[11] Patent Number: Plant 8,933

[45] Date of Patent: Oct. 11, 1994

[54] **HEATHER PLANT NAMED *ERICA PERSOLUTA* RUBY**

[75] Inventor: Bruno L. Imazio, Watsonville, Calif.

[73] Assignee: Imazio Nursery, Inc., Watsonville, Calif.

[21] Appl. No.: 153,458

[22] Filed: Nov. 16, 1993

[51] Int. Cl.[5] ..... A01H 5/00
[52] U.S. Cl. ..... Plt./54.1
[58] Field of Search ..... Plt. 54.1

[56] References Cited

PUBLICATIONS

Huxley, A., et al., "*Erica*", *The New RHS Dictionary of Gardening*, vol. 2, D to K, 1992, The Stockton Press, pp. 183–189.

*Primary Examiner*—James R. Feyrer
*Attorney, Agent, or Firm*—Christie, Parker & Hale

[57] ABSTRACT

A new and distinct cultivar of heather plant named Erica persoluta 'Ruby' having a blooming period that begins earlier than the variety 'Sunset' and later than the variety 'Flame'.

4 Drawing Sheets

SUMMARY OF THE INVENTION

The invention relates to a new and distinct variety of Ericacae. The varietal denomination of the new variety is *Erica persoluta* 'Ruby.'

This new heather variety was discovered by me from among thousands of self-pollinated and/or naturally cross-pollinated seedlings growing in a controlled cultivated field of the variety 'Sunset' (U.S. Plant Pat. No. 5,336) in my commercial nursery at Watsonville, Calif. 'Sunset' is believed to be the seed parent of the new variety but the pollen parent is unknown. About 22,000 of these seedlings were dug up, potted and placed in a lathhouse and by August of the same year, the healthiest survivors of the seedlings were planted in a controlled field by themselves.

The new variety was selected because of its vibrant red-magneta flower color and particular blooming time. *Erica persoluta* 'Ruby' begins blooming at about four weeks before the variety 'Sunset.' For example, in seasons where 'Sunset' begins blooming in early December, 'Ruby' begins blooming at the end of October to the beginning of November (in Watsonville, Calif.). Asexual reproduction from cuttings of the new variety, at the above noted location, has established that the characteristics of 'Ruby' are retained through successive propagations.

Comparison with Closest Variety

The closest commercial cultivar to the new variety of which I am aware is the seed parent, 'Sunset' (U.S. Plant Pat. No. 5,336). *Erica persoluta* 'Ruby' resembles 'Sunset' in the dark green color and shape of the foliage; however, the color of the 'Ruby' bloom is deeper and more red-magneta. The characteristics which distinguish the new variety form its seed parent are:

1. Blooming begins at least about four weeks before 'Sunset' under normal circumstances. In most seasons, this is the end of October to early November for the new variety and December for 'Sunset';

2. The shape of the 'Ruby' plant is much wider and more spread-out than that of the 'Sunset,' which is more upright and narrow;

3. The branches of both the new variety and 'Sunset' exhibit fullness, but 'Ruby' is wide and bushy at the base and tapers down to a slender tip, whereas 'Sunset' is narrow and slender from the base to the tip.

The variety 'Ruby' also differs from my variety *Erica persoluta* 'Flame', U.S. Plant Pat. No. 8,501, which, like 'Ruby', resembles in shape, color of foliage and fullness of the branches, *Erica persoluta* 'Sunset'. However, 'Ruby' is different from 'Flame' in the following respect:

1. The height of 'Ruby' plants is generally slightly shorter than 'Flame';

2. The fullness of the 'Ruby' stem tapers from the base to a narrow tip more quickly than 'Flame';

3. The color of the 'Ruby' bloom is more vibrant and more red;

4. 'Ruby' begins to bloom about four weeks later than 'Flame'; and

5. 'Ruby"s bloom is slightly smaller than 'Flame' and less round.

The most outstanding characteristics of the new variety is the time in which it blooms and its deep vibrant color, which is in demand in the Fall. Since 'Sunset' begins to bloom in December, and 'Flame' begins to bloom in early October, the new variety provides a longer period of availability of a cut flower with good length in this color range for the Fall season by filling the time gap.

BRIEF DESCRIPTION OF THE ILLUSTRATIONS

The accompanying illustrations show specimens of the new variety and comparison to its closest known commercial variety and seed parent, 'Erica Sunset.'

Figure 1:
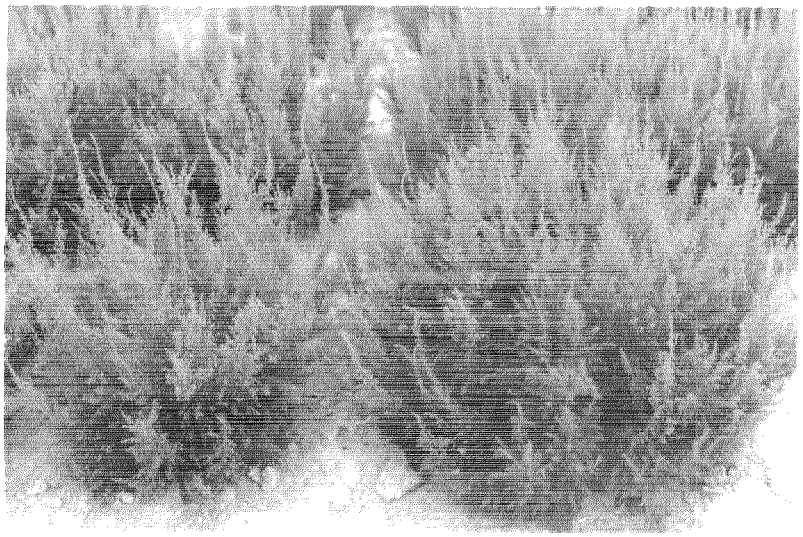
FIG. 1 is an illustration of the new variety taken in late October during overcast conditions and illustrates the shape of the branches and the plant.
Figure 2:
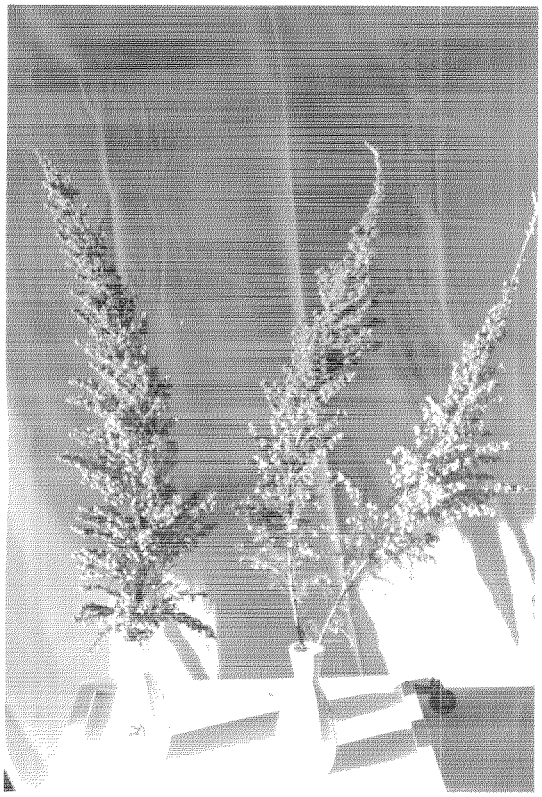
FIG. 2 shows three branches cut from a plant of *Erica persoluta* 'Ruby' and illustrates the overall shape and fullness of the branches.
Figure 3:
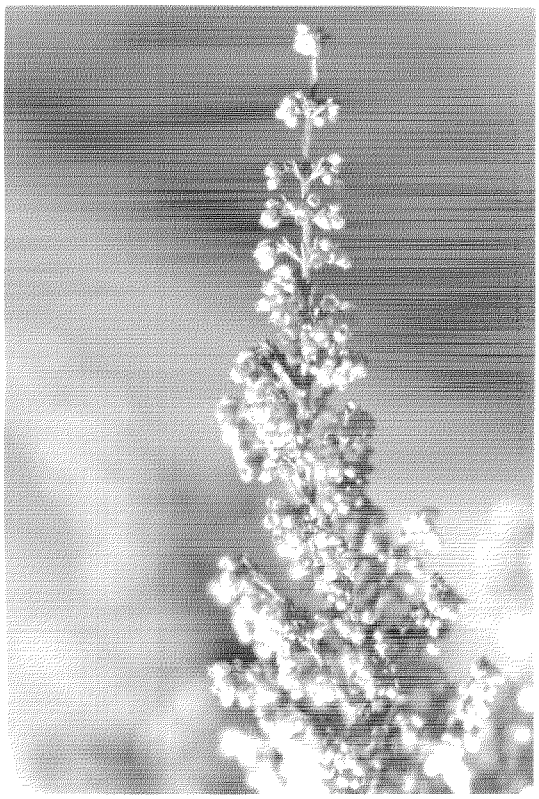
FIG. 3 is a closeup of one branch, giving a clear view of the shape, color, texture and density of the blooms and how they are borne.
Figure 4:
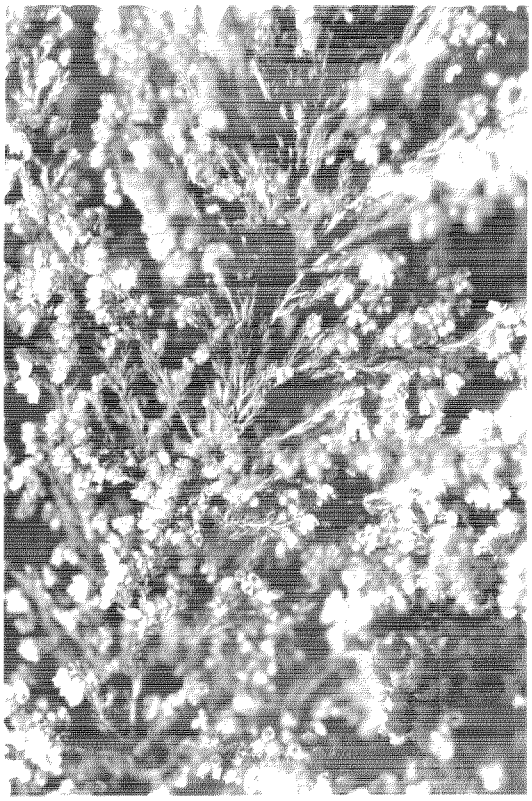
FIG. 4 is a color illustration showing the shape and color of the foliage.
Figure 5:
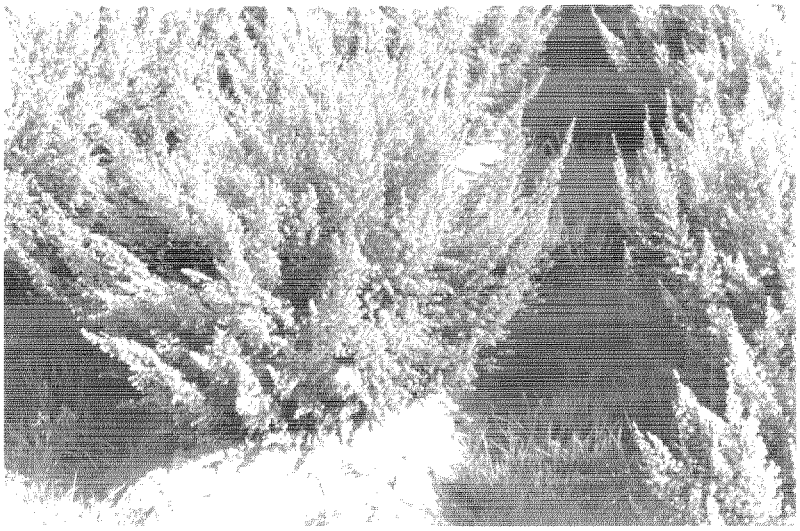
FIG. 5 is an illustration showing one plant in the field of 'Ruby' as it approaches full bloom.
Figure 6:
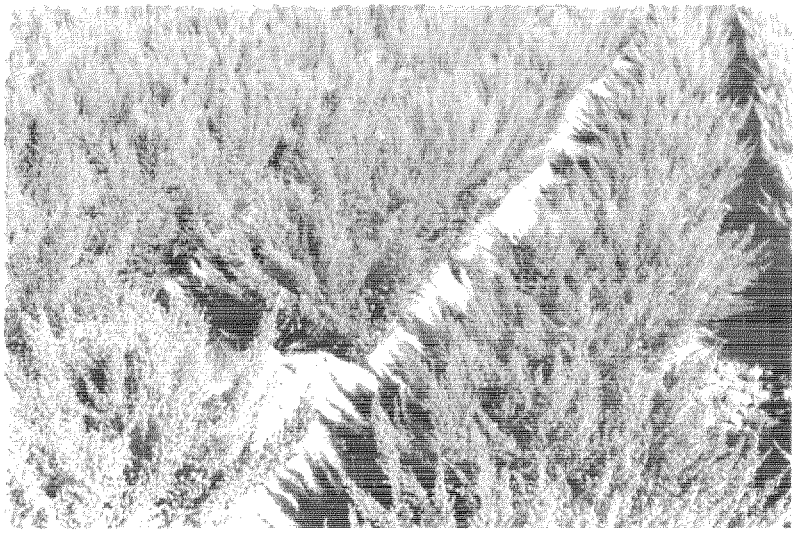
Figure 7:
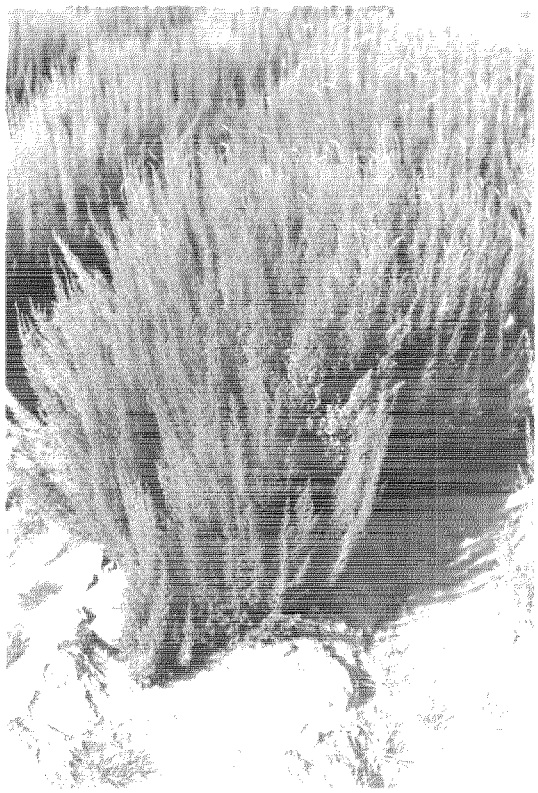

FIG. 6 is an illustration of a field of plants of the new variety near full bloom in mid-November; and FIG. 7 is an illustration of 'Sunset' heather in the field in mid-November and serves to illustrate the contrasting shape of the plant and branches of the seed parent, 'Sunset,' and also shows the difference between the blooming times of the new variety and 'Sunset,' which is still green with no blooms whereas the new variety is in full bloom (FIG. 6).

DETAILED DESCRIPTION OF THE NEW VARIETY

The following is a detailed description of *Erica persoluta* 'Ruby' from observation of field-grown plants in the Fall at Watsonville, Calif. The color terminology used in the accordance with The Royal Horticultural Society Colour Chart (R.H.S.C.C.), the colors specified being as accurate as can be reasonably obtained in an illustration of this character. It is understood that phenotypic expression may vary depending on light availability, climate and cultural conditions.

Origin: Seedling.
Parentage:
*Seed parent.*—'Sunset'.
*Pollen parent.*—Unknown.

PLANT

Form: Woody shrub, perennial.
Shape: Generally upright with stems curving to accommodate fullness of the plant, which is open, wide and bushy.
Height: About 2 to 2½ feet at maturity.
Main stem length: 2 to 2½ feet.
Branching: Thick, woody branches widely spaced due to fullness.
Growth: Vigorous, flexible wood.
Foliage:
*Size of leaf.*—About ⅛ inch long.
*Shape.*—Very narrow, about 1/16 inch or less.
*Color.*—Dark yellowish-green, near 141 A.
*Texture.*—Smooth.
Effects of weather: Plant can tolerate freezing temperatures for several hours. Temperatures over 90° F. stress the plant. Warm temperatures hasten bud formation and blooming. Extended wet weather causes flowers to decline more rapidly when in full bloom.

BUD

Size: Less than about ⅛ inch in diameter, less than about ¼ inch in length.
Shape: Globose urceolate.
Color: Red-violet or magneta, near 70A.
Rate of opening: Progressive and rapid from base of plant upwards to tip.

INFLORESCENCE

Blooming habit: Once annually, usually beginning late October/early November in Watsonville, Calif. and continuing for several weeks.
Size of bloom: About ¼ inch long, about ⅛ inch diameter.
Borne: Compound raceme with terminal clusters.
Shape: Globose urceolate.
Appearance: Satiny.
Color: Red-violet or magneta, near 70A.
Flower stem:
*Length.*—About ¼ to 4 inches (these are the side branches bearing the blooms).
*Color.*—Light brown.
*Strength.*—Supple.
Fragrance: Pungent-sweet.
Lasting quality:
*On plant.*—About 6 to 8 weeks.
*As cut flower.*—Up to about 4 weeks.
Discoloration: Can fade slightly in long exposure to bright sun in the field; and cut flower color darkens as stem and branch dehydrate.
Persistence: Blooms can persist long after stem ceases to draw water. Blooms persist on plant for extended period and turn brown.

I claim:

1. A new and distinct cultivar of heather plant, substantially as herein shown and described, characterized by its vibrant red-magneta flowers and by a blooming period which begins earlier than *Erica persoluta* 'Sunset' and later than *Erica persoluta* 'Flame.'

* * * * *